(12) United States Patent
Surti et al.

(10) Patent No.: US 8,388,617 B2
(45) Date of Patent: Mar. 5, 2013

(54) BARREL SYSTEM FOR USE WITH AN ENDOSCOPE

(75) Inventors: Vihar C. Surti, Winston-Salem, NC (US); Field F. Willingham, Decatur, GA (US)

(73) Assignees: Cook Medical Technologies LLC, Bloomington, IN (US); The General Hospital Corporation, Boston, MA (US)

( * ) Notice: Subject to any disclaimer, the term of this patent is extended or adjusted under 35 U.S.C. 154(b) by 669 days.

(21) Appl. No.: 12/568,222

(22) Filed: Sep. 28, 2009

(65) Prior Publication Data

US 2010/0191052 A1 Jul. 29, 2010

Related U.S. Application Data

(60) Provisional application No. 61/101,859, filed on Oct. 1, 2008.

(51) Int. Cl.
*A61B 18/14* (2006.01)

(52) U.S. Cl. .......................................................... 606/45

(58) Field of Classification Search ............... 606/45–50
See application file for complete search history.

(56) References Cited

U.S. PATENT DOCUMENTS

| 5,085,659 A | 2/1992 | Rydell |
| 6,086,583 A | 7/2000 | Ouchi |
| 7,198,625 B1 * | 4/2007 | Hui et al. ........................ 606/41 |
| 2003/0045873 A1 * | 3/2003 | Hinchliffe ....................... 606/47 |
| 2004/0158124 A1 | 8/2004 | Okada |
| 2005/0090709 A1 | 4/2005 | Okada et al. |
| 2006/0079873 A1 | 4/2006 | Scopton et al. |

FOREIGN PATENT DOCUMENTS

EP 1400214 3/2004

OTHER PUBLICATIONS

International Preliminary Report on Patentability for PCT/US2009/058575 mailed Apr. 14, 2011, 9 pgs.
International Search Report and Written Opinion for PCT/US2009/058575 dated Mar. 17, 2010, 16 pgs.

* cited by examiner

*Primary Examiner* — Michael Peffley
*Assistant Examiner* — Daniel Fowler
(74) *Attorney, Agent, or Firm* — Brinks Hofer Gilson & Lione (57) ABSTRACT

The present embodiments provide apparatus and methods for facilitating cauterization of tissue. In one embodiment, the apparatus comprises a proximal barrel and a distal barrel, which are coupled together and moveable with respect to one another. At least a portion of the proximal barrel may be coupled to an endoscope to secure the apparatus to the endoscope. At least one electrocautery member is disposed within a lumen of the distal barrel and configured to cauterize at least a segment of tissue pulled into a lumen of the proximal barrel and/or the lumen of the distal barrel.

21 Claims, 5 Drawing Sheets

BARREL SYSTEM FOR USE WITH AN ENDOSCOPE

PRIORITY CLAIM

This invention claims the benefit of priority of U.S. Provisional Application Ser. No. 61/101,859, entitled "Barrel System For Use With an Endoscope," filed Oct. 1, 2008, the disclosure of which is hereby incorporated by reference in its entirety.

TECHNICAL FIELD

The present invention relates generally to the field of medical devices, and more particularly, to a barrel system for use with an endoscope to facilitate cauterization of tissue.

BACKGROUND INFORMATION

There are various instances in which it may become necessary or desirable to cauterize a segment of a patient's tissue. For example, during an endoscopic procedure, it may become desirable to remove a segment of a mucosal layer of tissue from an underlying submucosal layer of tissue.

Typically, one or more cutting instruments, such as a needle knife, may be used to cauterize a segment of tissue. In an endoscopic procedure, the cutting instrument may be advanced through an auxiliary lumen of an endoscope. The cutting instrument then may be advanced beyond the distal end of the endoscope and actuated by supplying an electrical current to the tip of the instrument. Once heated, the cutting instrument may be positioned to engage and cauterize the target tissue. The cauterized tissue then may be captured and removed, for example, by using a forceps advanced through the auxiliary lumen of the endoscope.

When cutting instruments, such as needle knives, are used in the above-described manner, the result may yield an imprecise cauterization of tissue. In particular, when a sharp, pointed and/or heated instrument is advanced distal to the endoscope, a risk exists of improperly maneuvering the cutting instrument and therefore inadvertently cauterizing or searing healthy or non-target tissue. As an example, if the gallbladder is being separated from the liver using a cutting instrument such as a needle knife, it may be difficult to safely and precisely dissect the gallbladder using the extended cutting instrument.

Further, difficulties may arise when segregating mucosal tissue from underlying submucosal tissue. In these procedures, the extended cutting instrument is generally moved in a circular motion, which may increase the risk of incision to the underlying submucosal tissue. Moreover, if a snare or other mechanical instrument is used in lieu of a heated cutting instrument during such procedures, it also may yield an imprecise removal of tissue.

SUMMARY

The present invention provides apparatus and methods for facilitating cauterization of tissue. In one embodiment, the apparatus comprises a proximal barrel and a distal barrel, each having lumens. The proximal and distal barrels are coupled together and may be moveable with respect to one another. At least a portion of the proximal barrel is configured to be coupled to an endoscope to allow attachment of the apparatus to the endoscope. At least one electrocautery member is disposed within the lumen of the distal barrel and configured to cauterize at least a segment of tissue pulled into the lumen of the proximal and/or distal barrels.

In one embodiment, the proximal barrel may comprise proximal and distal regions. At least a portion of the proximal region of the proximal barrel is adapted to be coupled to the endoscope, for example, by being disposed around the exterior surface of the endoscope using an elastic fit. The distal barrel may be disposed over at least a portion of the distal region of the proximal barrel and configured for selective longitudinal movement with respect to the proximal barrel. At least one stop member may be disposed on the distal region of the proximal barrel to limit maximum advancement of the distal barrel with respect to the proximal barrel.

The cauterization member may comprise a portion extending circumferentially within an interior surface of the distal barrel, at a location near a distal end of the distal barrel, to at least partially surround tissue. The cauterization member is preferably configured so that only the tissue pulled into the lumen of the distal barrel and/or the proximal barrel, at a location proximal to the electrocautery member, may be cauterized.

The apparatus may further comprise an outer sheath secured to the proximal barrel, and an inner sheath secured to the distal barrel. The inner sheath may be disposed for longitudinal movement within the outer sheath. Further, a portion of the electrocautery member may be disposed within a portion of the inner sheath. In use, longitudinal movement of the inner sheath with respect to the outer sheath effects corresponding movement of the distal barrel with respect to the proximal barrel.

Advantageously, the amount of tissue that may be cauterized at one time may be varied by adjusting the positioning of the distal barrel with respect to the proximal barrel. In particular, by varying the positioning of the distal barrel with respect to the proximal barrel, various amounts of target tissue may be pulled into the one or more lumens of the telescopic barrel and subsequently excised by the cauterization member. Moreover, as yet another advantage, the retracted profile of the telescopic barrel may be relatively small to facilitate delivery into a patient's anatomy, then can be expanded, as needed, to remove a segment of tissue that is larger than the retracted profile of the telescopic barrel.

A suitable grasping device, such as a forceps, may be used in conjunction with the apparatus. The grasping device is preferably configured to be advanced through an auxiliary lumen of the endoscope to grasp and pull tissue into the lumen of the distal barrel and/or proximal barrel for cauterization and subsequent removal.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1A:
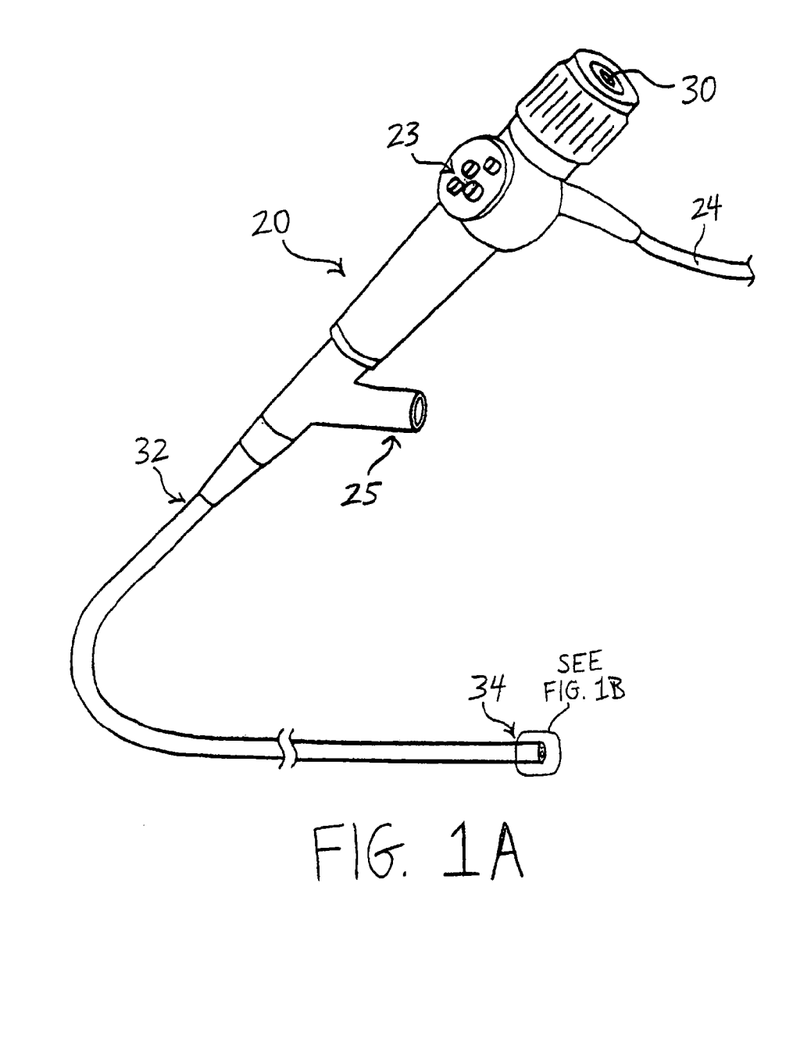
FIGS. 1A-1B are, respectively, a perspective view of an exemplary end-viewing endoscope and a close-up view of the distal region of the endoscope.
Figure 1B:
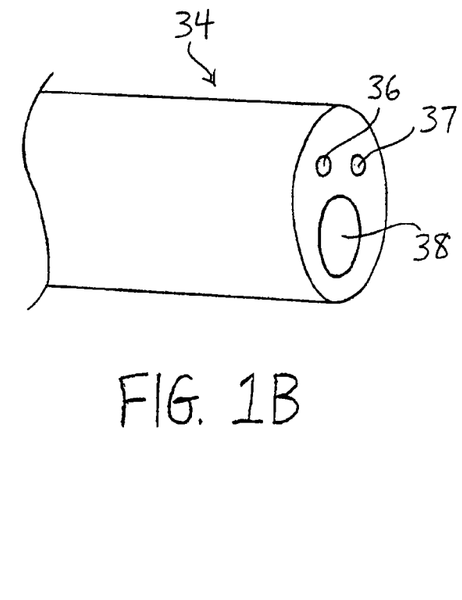

Referring now to FIGS. 1A-1B, an exemplary endoscope 20 is described, which may be used in conjunction with the telescopic barrel system described below. In FIG. 1A, the exemplary endoscope 20 comprises an end-viewing endoscope of known construction and having proximal and distal regions 32 and 34, respectively. The endoscope 20 may comprise fiber optic components 36 and 37 for illuminating and capturing an image distal to the endoscope 20, as depicted in FIG. 1B. A physician may view the images distal to the endoscope 20 using an eyepiece 30. A fiber optic cable 24 may be coupled between the endoscope 20 and a suitable light source. A control section 23 may be provided to maneuver the distal region 34 of the endoscope 20, and facilitate actuation of various components associated with the endoscope 20.

The endoscope 20 also may comprise an auxiliary lumen 38, as shown in FIG. 1B. An auxiliary port 25 may be placed in fluid communication with the auxiliary lumen 38, such that components advanced through the auxiliary port 25 are directed into the auxiliary lumen 38. The auxiliary lumen 38 may be sized to accommodate an array of medical components, such as a catheter, forceps, snare and the like. While one auxiliary lumen 38 is shown, additional lumens may be employed. Other features and components of the endoscope 20, and variations thereof, are generally known to those skilled in the art and are not critical to the present invention.

In a conventional procedure, the endoscope 20 may be advanced through a natural bodily lumen, such as the alimentary canal, to a position proximate a target location. A catheter or other medical devices then may be advanced through the auxiliary lumen 38 of the endoscope 20 to the target location. Optionally, a needle or other suitable device may be used to puncture through an organ or a gastrointestinal wall to provide translumenal endoscopic access to various additional bodily regions.

Figure 2:
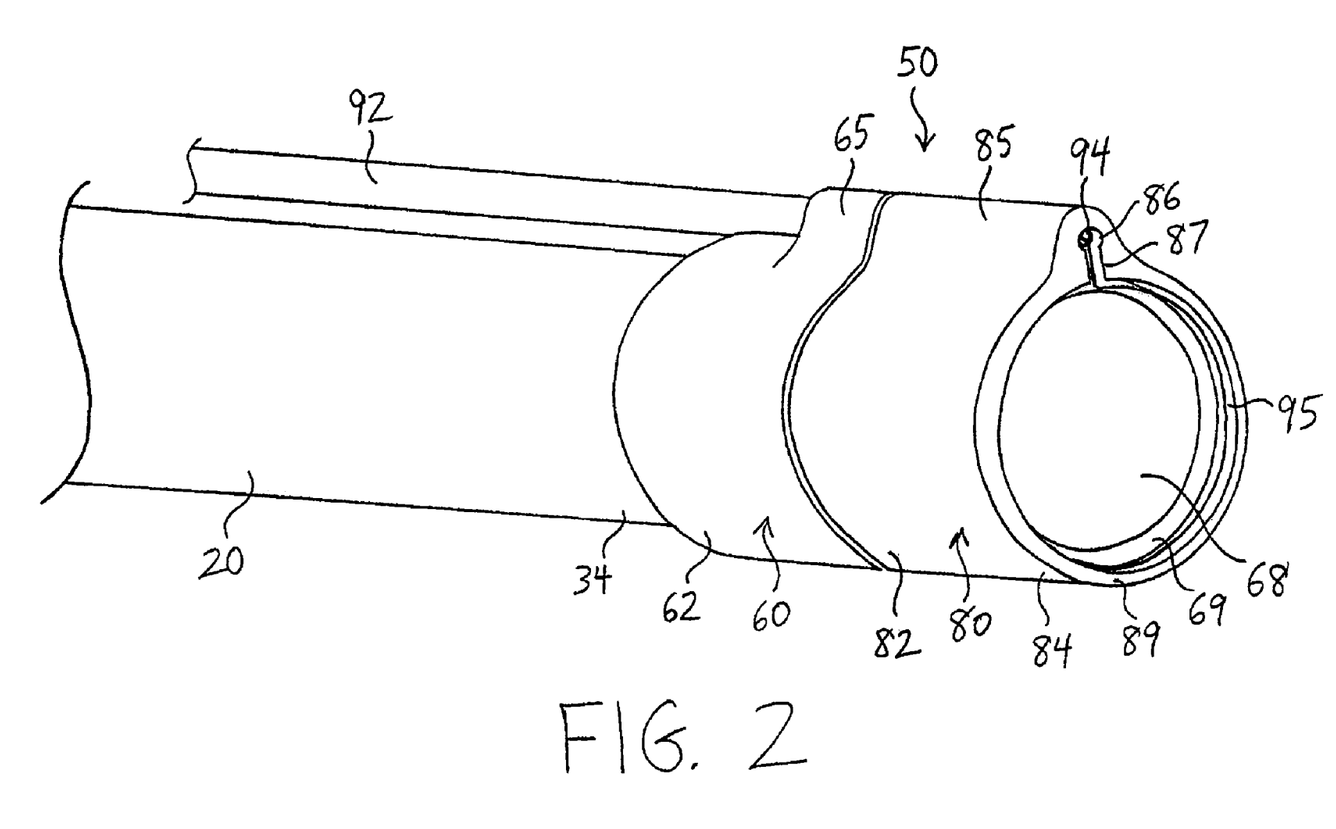
FIG. 2 is a perspective view of a telescopic barrel, which may be used in conjunction with the endoscope of FIG. 1, in a retracted state.

Referring now to FIG. 2, a first embodiment of a telescopic barrel 50 according to the present invention is described. In this embodiment, the telescopic barrel 50 generally comprises a proximal barrel 60 and a distal barrel 80. As explained in further detail below, the proximal barrel 60 may be coupled to the distal region 34 of the endoscope 20, while the distal barrel 80 may comprise a cauterization member 95 configured to treat tissue. The distal barrel 80 may be selectively longitudinally advanced or retracted with respect to the proximal barrel 60.

Figure 3:
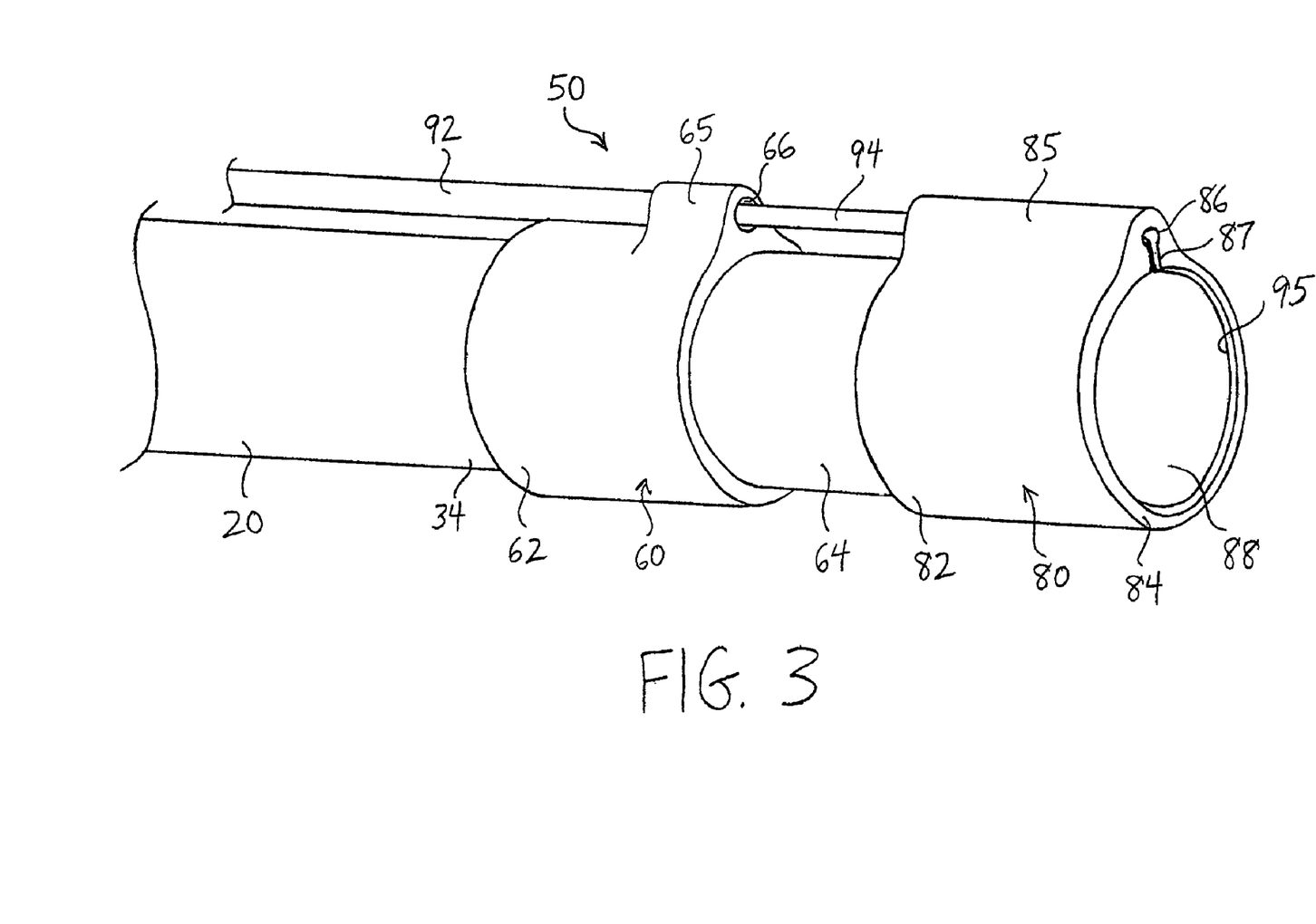
FIG. 3 is a perspective view of the telescopic barrel of FIG. 2 in an expanded state.
Figure 4:
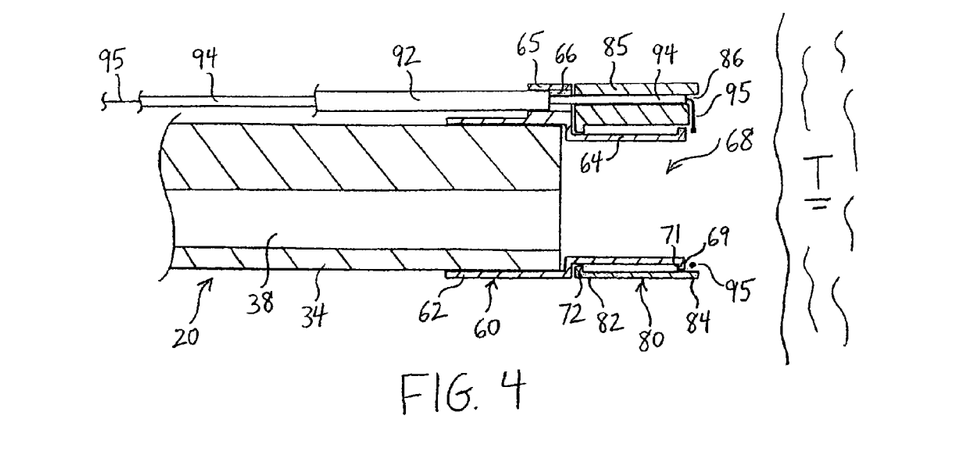
FIG. 4 is a side-sectional view of the telescopic barrel of FIG. 2 in the retracted state, with an outer sheath and inner sheath shown from a side perspective view for illustrative purposes.
Figure 5:
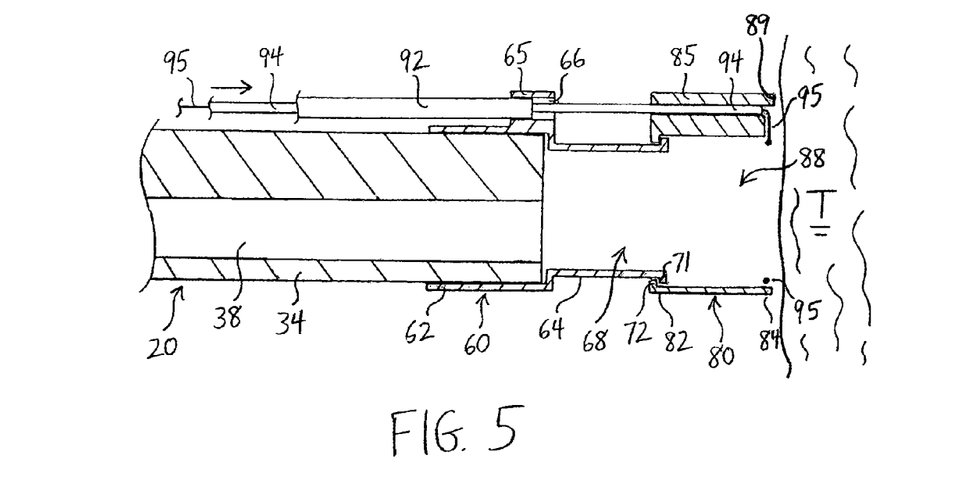
FIG. 5 is a side-sectional view of the telescopic barrel of FIG. 3 in the expanded state, with an outer sheath and inner sheath shown from a side perspective view for illustrative purposes.

In one embodiment, the proximal barrel 60 comprises proximal and distal regions 62 and 64, respectively, as best seen in FIGS. 3-5. The proximal region 62 may be coupled to the distal region 34 of the endoscope 20. Preferably, at least a portion of the proximal region 62 of the proximal barrel 60 is disposed about an exterior surface of the endoscope 20, as shown in FIGS. 2-5.

In one embodiment, at least a portion of the proximal region 62 comprises an elastic member having a first inner diameter in a relaxed state, and a second, slightly larger inner diameter when in an expanded state. If the proximal region 62 is elastic, it may be sized such that its inner diameter in the relaxed state is slightly smaller than an exterior diameter of the endoscope 20, but its inner diameter in the expanded state is slightly larger than the exterior diameter of the endoscope 20. This configuration allows at least the proximal region 62 of the proximal barrel 60 to elastically expand to be disposed over the distal region 34 of the endoscope 20. Once in place, the proximal region 62 will be allowed to return to its relaxed state, thereby securely engaging the proximal barrel 60 around the exterior surface of the endoscope 20 using a frictional fit, as shown in FIGS. 2-5. An interior surface of the proximal portion 62 may comprise a texture or material, such as rubber, configured to increase the frictional fit with the exterior surface of the endoscope 20.

If desired, a securing means may be applied to secure a portion of the proximal barrel 60 directly to an exterior surface of the endoscope 20 to prohibit movement of the proximal barrel 60 with respect to the endoscope 20. For example, the securing means may comprise an adhesive tape, heat-shrink tubing, one or more tie-down bands, cable-ties, and the like. The securing means may be configured and disposed so as to not interfere with movement of the endoscope 20 through the patient. Further details of an exemplary securing means and techniques for securing a component, such as the proximal barrel 60, to an exterior surface of an endoscope are explained in applicants' co-pending U.S. patent application Ser. No. 11/747,570, filed May 11, 2007, the disclosure of which is hereby incorporated by reference in its entirety.

The distal region 64 of the proximal barrel 60 may comprise a generally tubular shape having a working lumen 68, as best seen in FIGS. 4-5. Inner and outers diameter at the distal region 64 of the proximal barrel 60 may be slightly smaller than corresponding diameters of the proximal region 62 of the proximal barrel 60, as depicted in FIGS. 3-5. Alternatively, the inner diameter of the distal region 64 may be configured to be substantially flush with the outer diameter of the endoscope 20. While the dimensions may be varied, the distal region 64 preferably does not interfere with the advancement of components through the auxiliary lumen 38 or the function of fiber optic components 36 and 37 of the endoscope 20, as depicted in FIGS. 4-5.

The proximal and distal regions 62 and 64 of the proximal barrel 60 may be integrally formed, as generally depicted in FIGS. 4-5, or alternatively may comprise two separate generally tubular members that are affixed or coupled together. Accordingly, the proximal barrel 60 may comprise one or more tubular members that are used in conjunction with the distal barrel 80 to achieve the objectives described in the present application and as explained in further detail below.

The distal barrel 80 comprises proximal and distal regions 82 and 84, respectively. In the retracted state, shown in FIGS. 2 and 4, the proximal region 82 of the distal barrel 80 may abut the proximal region 62 of the proximal barrel 60. The proximal and distal barrels 60 and 80 may comprise the same outer diameters, such that the proximal and distal barrels 60 and 80 lie substantially flush to one another in the retracted state, as shown in FIGS. 2 and 4.

The distal barrel 80 preferably comprises an inner diameter that is slightly larger than an outer diameter of the distal region 64 of the proximal barrel 60, as shown in FIGS. 4-5. Accordingly, the distal barrel 80 is configured for longitudinal movement with respect to the distal region 64 of the proximal barrel 60.

The proximal region 82 of the distal barrel 80 may comprise an inwardly-directed stop member 72. The stop member 72 is configured to abut a flared outwardly-directed stop member 71 on the distal region 64 of the proximal barrel 60 to limit the maximum distal advancement of the distal barrel 80 and prevent detachment of the distal barrel 80 from proximal barrel 60, and consequently from the endoscope 20.

At least one cauterization member 95 may be disposed within the distal region 84 of the distal barrel 80, as shown in FIGS. 2-5. In one example, at least a portion of the cauterization member 95 comprises a portion extending circumferentially within an interior surface of the distal barrel 80, at a location near a distal end of the distal barrel 80, to at least partially surround tissue. The cauterization member 95 may comprise a circular configuration configured to be approximately the same size as, or slightly smaller than, an inner surface of the distal barrel 80. In the retracted state, shown in FIGS. 2 and 4, the cauterization member 95 may be disposed just distal to a distal tip 69 of the proximal barrel 60. Further, the cauterization member 95 preferably is disposed entirely within inner confines of the distal barrel 80 at a location proximal to a distal tip 89 of the distal barrel 80. Accordingly, the cauterization member 95 may cauterize tissue that has been pulled within the telescopic barrel 50, but not surrounding tissue, as explained in further detail below.

In one embodiment, the cauterization member 95 may comprise one or more wires that may be heated using an electric current. The cauterization member 95 may be fabricated from any electrically conductive material, including stainless steel. Alternatively, it may be fabricated from a shape memory alloy such as nitinol. An electrosurgical generator may be coupled to a proximal region of the cauterization member 95 to provide an electrical energy sufficient to cauterize the tissue. In one embodiment, the cauterization member 95 may be insulated along a portion of its length using an inner sheath 94, as explained further below.

Movement of the proximal and distal barrels 60 and 80 with respect to one another may be actuated in various ways. In one embodiment, the proximal and distal barrels are actuated using an outer sheath 92 and an inner sheath 94. As shown in FIGS. 3-5, the outer sheath 92 may be affixed to the proximal barrel 60, while the inner sheath 94 may be affixed to the distal barrel 80. The inner sheath 94 has an outer diameter that is smaller than an inner diameter of the outer sheath 92, thereby permitting longitudinal movement of the inner sheath 94 with respect to the outer sheath 92. Further, the inner sheath 94 may comprise an inner diameter configured to receive at least a portion of the cauterization member 95, thereby insulating at least a portion of the cauterization member 95 along its length.

The outer sheath 92 and the inner sheath 94 may be coupled to flared regions 65 and 85 of the proximal and distal barrels 60 and 80, respectively. In one embodiment, the flared region 65 of the proximal barrel 60 comprises a bore 66 disposed therethrough, as shown in FIGS. 3-5. The outer sheath 92 is placed in communication with the bore 66. The outer sheath 92 may be disposed at least partially within the bore 66, as depicted in FIGS. 4-5. The outer sheath 92 is securely attached to the proximal barrel 60, and since the proximal barrel 60 is secured to the endoscope 20, the outer sheath 92 is effectively secured against longitudinal movement relative to the endoscope 20.

The flared region 85 of the distal barrel 80 similarly comprises a bore 86 disposed therethrough, as shown in FIGS. 2-5. The inner sheath 94 is disposed through the outer sheath 92, and extends distal to the outer sheath 92 such that the inner sheath 94 is placed in communication with the bore 86. The inner sheath 94 preferably is disposed at least partially within the bore 86, as depicted in FIGS. 4-5. The inner sheath 94 is securely attached to the distal barrel 80. Therefore, distal advancement of the inner sheath 94 with respect to the outer sheath 92 effects corresponding movement of the distal barrel 80 with respect to the proximal barrel 60 and the endoscope 20.

If desired, one or more securing means may be applied to secure one or more portions of the outer sheath 92 directly to an exterior surface of the endoscope 20 to prohibit movement of the outer sheath 92 with respect to the endoscope 20. As noted above, a suitable securing means may comprise an adhesive tape, heat-shrink tubing, one or more tie-down bands, cable-ties, and the like. Such a securing means may reduce potential interference caused by the outer sheath 92 as the endoscope 20 is moved through the patient.

An exemplary method of using the telescopic barrel 50 will be described to cauterize mucosal tissue T away from submucosal tissue in a safe and effective manner. In a first step, the endoscope 20 may be retrofitted using the telescopic barrel 50 by securing at least a portion of the proximal portion 62 of the proximal barrel 60 to the endoscope 20. For example, the proximal portion 62 may be disposed over the distal region 34 of the endoscope 20 and secured using elastic properties of the proximal portion 62 and/or an external securing means. A portion of the outer sheath 92 also may be secured to the endoscope 20 using a securing means at one or more locations, as noted above.

The endoscope 20 may be advanced to a desired target site using suitable imaging techniques, such as the fiber optic components 36 and 37, an ultrasound transducer, fluoroscopic techniques in conjunction with radiopaque bands, and the like. Preferably, the endoscope 20 is advanced towards the target site with the distal barrel 80 in the retracted state shown in FIGS. 2 and 4, such that the proximal and distal barrels 60 and 80 lie substantially flush to one another during delivery of the device.

Once the physician has properly positioned the device adjacent to the mucosal tissue T to be cauterized, the physician may determine whether or not to advance the distal barrel 80 with respect to the proximal barrel 60. If the distal barrel 80 is not advanced, then the maximum amount of tissue that may be cauterized by the cauterization member 95 is approximately the same as, or slightly greater than, the volume of the working lumen 68 within the distal region 64 of the proximal barrel 60, as shown in FIG. 4. If the distal barrel 80 is fully advanced, then the maximum amount of tissue that may be cauterized is approximately the combined volume of the working lumen 68 within the distal region 64 of the proximal barrel 60, plus the working lumen 88 within the distal barrel 80, as shown in FIG. 5. The physician also may choose to move the distal barrel 80 to any intermediate position between most proximal and distal positions shown in FIGS. 4 and 5 to achieve the desired volume.

As noted above, the distal barrel 80 may be advanced the desired distance with respect to the proximal barrel 60 by distally advancing the inner sheath 94. Since the inner sheath 94 is securely attached to the flared region 85 of the distal barrel 80, distal advancement of the inner sheath 94 with respect to the outer sheath 92 effects corresponding distal advancement of the distal barrel 80 with respect to the proximal barrel 60, as shown in the expanded states of FIGS. 3 and 5. It should be noted that the maximum distal advancement of the distal barrel 80 with respect to the proximal barrel 60 is limited by the stop member 72 of the distal barrel 80 abutting the stop member 71 of the proximal barrel 60, as shown in FIG. 5.

Figure 6:
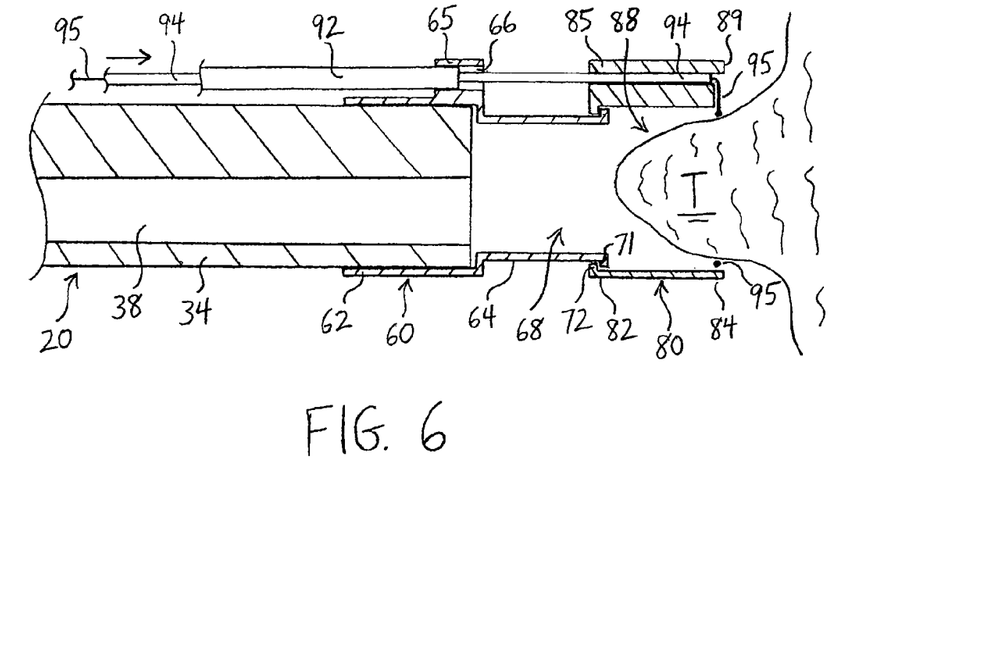
FIG. 6 is a side-sectional view of the telescopic barrel having tissue disposed within at least a lumen of a distal barrel.

When the distal barrel 80 is positioned at a desired longitudinal location with respect to the proximal barrel 60, as depicted in FIG. 5, a forceps or other suitable grasping instrument may be advanced through the auxiliary lumen 38 of the endoscope 20 and positioned distal to the endoscope to grasp the targeted mucosal tissue T. The forceps or other instrument may be actuated to grasp the tissue T and then retracted to pull at least a selected portion of the targeted mucosal tissue T into the working lumen 88 within the distal barrel 80 and/or the working lumen 68 within the distal region 64 of the proximal barrel 60, as depicted in FIG. 6. Alternatively, suction may be applied via the auxiliary lumen 38 to draw the target tissue T into the proximal and/or distal barrels 60 and 80. Advantageously, the fiber optic components 36 and 37 may illuminate and capture an image distal to the endoscope 20 during this process.

It should be noted that the target tissue T may be drawn into substantially the entire interior volume of both the proximal and/or distal barrels 60 and 80, or alternatively, just a portion of the proximal and/or distal barrels 60 and 80, as depicted in FIG. 6. If suction is applied via the auxiliary lumen 38, then the target tissue T may be drawn substantially into the entire interior volume of the proximal and/or distal barrels 60 and 80 via the suction. Further, it should be noted that the distal tip 89 of the distal barrel 80 may abut the tissue at this time, or may be disposed just proximal to the tissue.

When the desired amount tissue T is captured and properly positioned with respect to the cauterization member 95, as depicted in FIG. 6, the cauterization member 95 may be actuated to incise the mucosal tissue T within the telescopic barrel 50 at a location proximal to the cauterization member 95, thereby separating the mucosal tissue T from the submucosal tissue.

Advantageously, using the telescopic barrel 50 of the present embodiments, only the desired mucosal tissue T that is pulled within the inner confines of the distal barrel 80 and/or the proximal barrel 60 are severed. Surrounding mucosal tissue, as well as submucosal tissue, will not be inadvertently incised by the cauterization member 50. The risk of inadvertently incising unwanted tissue may be substantially reduced or eliminated.

Further, the amount of tissue T that may be cauterized at one time may be varied by adjusting the positioning of the distal barrel 80 with respect to the proximal barrel 60. More specifically, tissue T may be pulled into the working lumen 88 within the distal barrel 80 and/or the working lumen 68 within the distal region 64 of the proximal barrel 60. In the retracted state of FIGS. 2 and 4, tissue pulled into the telescopic barrel 50 is disposed substantially within the working lumen 68 of the proximal barrel 60. However, when the distal barrel 80 is advanced distally and into the expanded state of FIGS. 3 and 5, tissue may be pulled into both the working lumen 88 within the distal barrel 80 and the working lumen 68 within the distal region 64 of the proximal barrel 60. Alternatively, in the expanded state of FIGS. 3 and 5, tissue may only be pulled slightly into the barrel such that the tissue lies only within the working lumen 88 within the distal barrel 80. Accordingly, by varying the positioning of the distal barrel 80 with respect to the proximal barrel 60, various amounts of target tissue may be pulled into the one or more working lumens of the telescopic barrel 50 and subsequently excised by the cauterization member 95. Moreover, as yet another advantage, the retracted profile of the telescopic barrel 50 may be relatively small to facilitate delivery into a patient's anatomy, then can be expanded, as needed, to remove a segment of tissue that is larger than the retracted profile of the telescopic barrel 50.

In another exemplary procedure, the telescopic barrel 50 may be used to segregate an organ from surrounding tissue. For example, to remove an organ such as the gallbladder, portions of the organ may be pulled into the working lumen of the distal barrel 80 and/or the proximal barrel 60, then safely dissected and separated from the liver.

The above-referenced procedures are only a few examples in which the telescopic barrel 50 may be used, as it will be apparent that numerous other procedures are possible. Further, a telescopic barrel 50 provided in accordance with the present invention may be used in conjunction with an array of existing commercial endoscopes.

In an alternative embodiment, the barrel system need not comprise the telescopic feature described herein. In this alternative embodiment, a single barrel having first and second portions may be provided. The first portion is adapted to be coupled to the endoscope 20, while the second portion extends distal to the endoscope 20 and forms a working lumen therein. The electrocautery member 95 is disposed within the working lumen of the barrel at a location distal to the endoscope and configured to incise tissue pulled into the working lumen at a location proximal to the electrocautery member. Therefore, in this embodiment, a barrel member, which is not telescopic, is nevertheless configured to be coupled to an endoscope and configured to pull tissue into the barrel to safely and effectively incise tissue.

Figure 7:
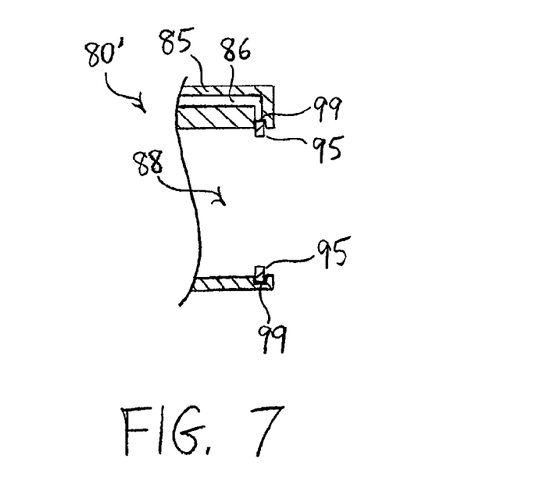
FIG. 7 is a side-sectional view of a portion of an alternative distal barrel.

Further, the configuration of the distal barrel 80 and/or cauterization member 95 may be varied. For example, referring to FIG. 7, an alternative distal barrel 80' may comprise a circumferential groove 99, which is adapted to receive a washer-shaped cauterization member 95. The cauterization member 95 may be placed in communication with a source of electric current via the bore 86 formed in the flared region 85 of the distal barrel 80'. Still further configurations of the distal barrel 80 and the cauterization member 95 are within the scope of the present invention.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. Apparatus for facilitating cauterization of tissue, the apparatus comprising:
    a proximal barrel adapted to be slid over a distal end of an endoscope and comprising a lumen disposed therein;
    a distal barrel coupled to the proximal barrel, the distal barrel comprising a lumen disposed therein, wherein the distal barrel is moveable longitudinally with respect to the proximal barrel; and
    an electrocautery member disposed within the lumen of the distal barrel and configured to cauterize a segment of tissue disposed within at least one of the lumen of the distal barrel and the lumen of the proximal barrel.

2. The apparatus of claim 1 wherein the electrocautery member comprises a portion extending circumferentially within an interior surface of the distal barrel, at a location near a distal end of the distal barrel, to at least partially surround tissue.

3. The apparatus of claim 1 wherein the electrocautery member comprises a loop operably connected to a distal end of a wire, a proximal end of the wire being configured to be operably connected to a source of electric current.

4. The apparatus of claim 1 wherein the distal barrel is moveable between an extended state and a retracted state, the distal barrel having a distal edge that is positioned substantially adjacent to a distal edge of the proximal barrel in the retracted state, and wherein a segment of tissue is adapted to be in contact with an inner surface of the proximal barrel in the retracted state.

5. The apparatus of claim 1 wherein the distal barrel may be advanced distally with respect to the proximal barrel from a retracted state to an expanded state, and wherein a segment of tissue is adapted to be disposed through a full length of the distal barrel and into at least a portion of the proximal barrel in the expanded state.

6. The apparatus of claim 1 wherein the proximal barrel comprises proximal and distal regions, wherein at least a portion of the proximal region is adapted to be disposed around an exterior surface of an endoscope, and wherein the distal barrel is disposed for longitudinal movement over at least a portion of the distal region of the proximal barrel.

7. The apparatus of claim 6 wherein the portion of the proximal region that is adapted to be disposed about the exterior surface of an endoscope comprises an elastic member having a larger diameter state adapted to be placed over an endoscope and a smaller diameter state that permits the proximal barrel to be elastically secured about the exterior surface of an endoscope.

8. The apparatus of claim 6 wherein the distal region of the proximal barrel comprises a stop member adapted to limit maximum distal movement of the distal barrel.

9. The apparatus of claim 1 further comprising:
an outer sheath secured to the proximal barrel; and
an inner sheath secured to the distal barrel, wherein the inner sheath is disposed for longitudinal movement within the outer sheath, and wherein longitudinal movement of the inner sheath with respect to the outer sheath effects corresponding movement of the distal barrel with respect to the proximal barrel.

10. The apparatus of claim 9 wherein the inner sheath comprises a lumen adapted to receive at least a portion of the at least one electrocautery member.

11. The apparatus of claim 9 wherein the proximal barrel comprises a flared region having a bore configured to receive a portion of the outer sheath, and the distal barrel comprises a flared region having a bore configured to receive a portion of the inner sheath.

12. The apparatus of claim 1 further comprising an endoscope, wherein the proximal barrel is disposed on a distal end of the endoscope.

13. A method for facilitating cauterization of tissue, the method comprising:
providing apparatus comprising a proximal barrel and a distal barrel, wherein the distal barrel is coupled to a portion of the proximal barrel and configured for longitudinal movement with respect to the proximal barrel;
coupling at least a portion of the proximal barrel to an endoscope;
disposing tissue within at least one of a lumen of the proximal barrel and a lumen of the distal barrel; and
using at least one electrocautery member disposed within the lumen of the distal barrel to cauterize the tissue disposed within the at least one of the lumen of the distal barrel and the lumen of the proximal barrel.

14. The method of claim 13 wherein the step of coupling the proximal barrel to an endoscope comprises elastically securing at least a portion of the proximal barrel around an exterior surface of the endoscope.

15. The method of claim 13 further comprising the step of using a stop member disposed on a distal region of the proximal barrel to limit maximum distal movement of the distal barrel.

16. The method of claim 13 further comprising
securing an outer sheath to the proximal barrel;
securing an inner sheath to the distal barrel, wherein the inner sheath is disposed for longitudinal movement within the outer sheath; and
longitudinally moving the inner sheath with respect to the outer sheath to effect corresponding movement of the distal barrel with respect to the proximal barrel.

17. Apparatus for facilitating cauterization of tissue, the apparatus comprising:
a proximal barrel adapted to be coupled to an endoscope and comprising a lumen disposed therein;
a distal barrel coupled to the proximal barrel, the distal barrel comprising a lumen disposed therein, wherein the distal barrel is moveable longitudinally with respect to the proximal barrel; and
an electrocautery member disposed within the lumen of the distal barrel and configured to cauterize a segment of tissue disposed within at least one of the lumen of the distal barrel and the lumen of the proximal barrel,
where the proximal barrel and the distal barrel are joined in a non-detachable telescoping manner.

18. The apparatus of claim 17 wherein the electrocautery member comprises a portion extending circumferentially within an interior surface of the distal barrel, at a location near a distal end of the distal barrel, to at least partially surround tissue.

19. The apparatus of claim 18 further comprising:
an outer sheath secured to the proximal barrel; and
an inner sheath secured to the distal barrel, wherein the inner sheath is disposed for longitudinal movement within the outer sheath, and wherein longitudinal movement of the inner sheath with respect to the outer sheath effects corresponding movement of the distal barrel with respect to the proximal barrel.

20. Apparatus for facilitating cauterization of tissue, the apparatus comprising:
a proximal barrel adapted to be coupled to an endoscope and comprising a lumen disposed therein;
a distal barrel coupled to the proximal barrel, the distal barrel comprising a lumen disposed therein, wherein the distal barrel is moveable longitudinally with respect to the proximal barrel; and
an electrocautery member disposed within the lumen of the distal barrel and configured to cauterize a segment of tissue disposed within at least one of the lumen of the distal barrel and the lumen of the proximal barrel,
wherein the distal barrel is moveable between an extended state and a retracted state, and wherein a segment of tissue is adapted to be in contact with an inner surface of the proximal barrel in the retracted state.

21. Apparatus for facilitating cauterization of tissue, the apparatus comprising:
a proximal barrel adapted to be coupled to an endoscope and comprising a lumen disposed therein;

a distal barrel coupled to the proximal barrel, the distal barrel comprising a lumen disposed therein, wherein the distal barrel is moveable longitudinally with respect to the proximal barrel; and an electrocautery member disposed within the lumen of the distal barrel and configured to cauterize a segment of tissue disposed within at least one of the lumen of the distal barrel and the lumen of the proximal barrel, wherein the distal barrel may be advanced distally with respect to the proximal barrel from a retracted state to an expanded state, and wherein a segment of tissue is adapted to be disposed through a full length of the distal barrel and into at least a portion of the proximal barrel in the expanded state.

* * * * *